United States Patent [19]

Kiozpeoplou

[11] Patent Number: 4,487,757

[45] Date of Patent: Dec. 11, 1984

[54] DISPENSING CONTAINER OF TOOTHPASTE WHICH EFFERVESCES DURING TOOTHBRUSHING

[75] Inventor: Diana K. Kiozpeoplou, Somerville, N.J.

[73] Assignee: Colgate-Palmolive Company, New York, N.Y.

[21] Appl. No.: 443,072

[22] Filed: Nov. 22, 1982

Related U.S. Application Data

[63] Continuation-in-part of Ser. No. 334,994, Dec. 28, 1981, abandoned.

[51] Int. Cl.$^3$ .......................... A61K 7/16; B65D 35/22
[52] U.S. Cl. ........................................ 424/7.1; 424/44; 424/49
[58] Field of Search ...................... 424/7.1, 44, 49–58; 222/94

[56] References Cited

U.S. PATENT DOCUMENTS

| | | | |
|---|---|---|---|
| 1,297,494 | 3/1919 | Rhein | 424/44 |
| 1,535,529 | 4/1925 | Hopkins | 424/44 |
| 2,035,267 | 3/1936 | Fleischman | 424/53 |
| 2,789,731 | 4/1957 | Marraffino | 222/129 |
| 3,087,857 | 4/1963 | Davis et al. | 424/55 X |
| 3,121,623 | 2/1964 | Nesin | 51/293 |
| 3,577,521 | 5/1971 | Scheller et al. | 424/55 |
| 3,881,529 | 5/1975 | Mannara | 141/100 |
| 3,935,305 | 1/1976 | Delaney et al. | 424/49 |
| 3,937,321 | 2/1976 | Delaney et al. | 424/49 |
| 3,937,803 | 2/1976 | Delaney et al. | 424/49 |
| 3,937,804 | 2/1976 | Delaney et al. | 424/49 |
| 3,943,240 | 3/1976 | Delaney et al. | 424/49 |
| 3,966,863 | 6/1976 | Forward et al. | 424/49 |
| 3,980,767 | 9/1976 | Chown et al. | 424/49 |
| 4,066,745 | 1/1978 | Tomlinson et al. | 424/44 |
| 4,098,435 | 7/1978 | Weyn | 222/94 |
| 4,160,022 | 7/1979 | Delaney et al. | 424/52 |
| 4,211,341 | 7/1980 | Weyn | 222/94 |
| 4,328,205 | 5/1982 | Taylor | 424/49 |

FOREIGN PATENT DOCUMENTS

| | | |
|---|---|---|
| 2327762 | 5/1977 | France ........................ 424/44 |
| 1492660 | 11/1977 | United Kingdom . |
| 1565672 | 4/1980 | United Kingdom . |

*Primary Examiner*—Shep K. Rose
*Attorney, Agent, or Firm*—Robert L. Stone; Murray M. Grill; Herbert S. Sylvester

[57] ABSTRACT

A container of toothpaste comprises two portions, one containing a stabilized alkali metal bicarbonate and the other containing an acid or acid salt which is reactive with the bicarbonate to produce carbon dioxide upon simultaneous dispensing of both portions of the toothpaste. Reaction of the bicarbonate and the acidic material, and resulting effervescence are avoided during storage by maintaining the two portions of the toothpaste in separated sections of the toothpaste container, from which they may be dispensed together. Upon dispensing, as by extrusion of both portions from a collapsible tube, they contact each other with little or no effervescent reaction at the interface of the two phases, but effervesce strongly during intimate mixing of the portions during toothbrushing. Preferably the toothpaste is extruded from the tube as an attractive plural-colored striped or variegated ribbon, with the different portions being differently colored to produce the striped or other plural-colored appearance.

16 Claims, 3 Drawing Figures

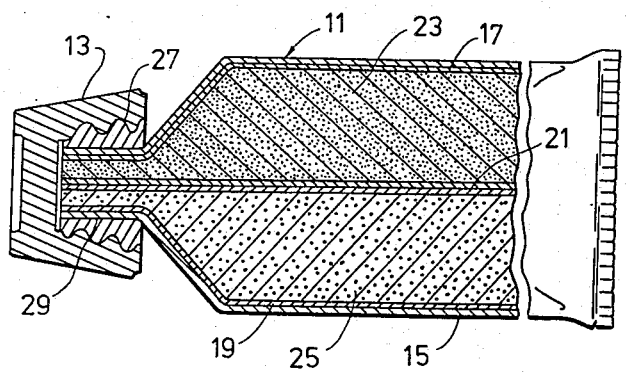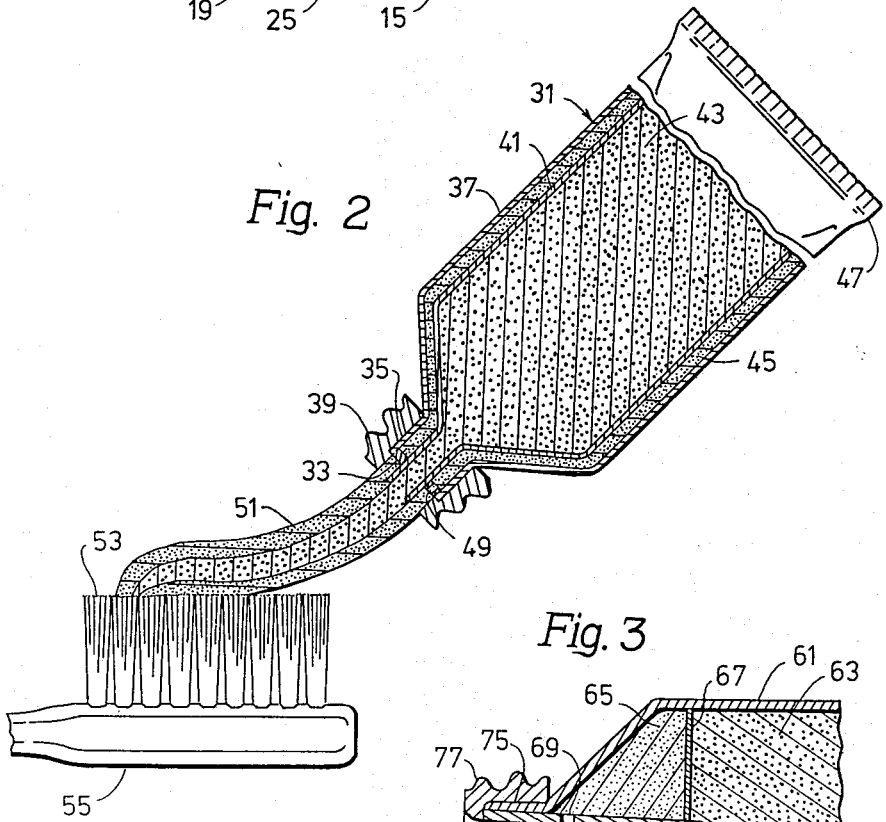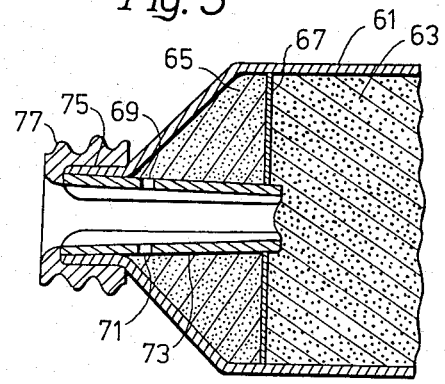

DISPENSING CONTAINER OF TOOTHPASTE WHICH EFFERVESCES DURING TOOTHBRUSHING

This application is a continuation-in-part of my application Ser. No. 334,994, filed Dec. 28, 1981, abandoned.

This invention relates to containers of detifrices. More particularly, it relates to tubes of toothpastes, which contain separated reactive constituents, which interact to develop effervescence when they are brought into intimate contact during toothbrushing.

Sodium bicarbonate, also known as baking soda, has been employed for various purposes and is a common household product. It has been recommended for use in dentrifrices, such as toothpastes and tooth powders.

Bringing to market a practical and effective "baking soda toothpaste" which is acceptable to consumers has presented many special problems to inventors and manufacturers. Among factors which have to be considered are the unique characteristics of baking soda, including chemical, physical and cosmetic properties, when it is employed as a toothpaste component. For example, it is comparatively water soluble and, unless stabilized, tends to release carbon dioxide in an aqueous system. It is salty to the taste, and taste is one of the more important considerations in the purchase and use of all oral and dental items. Other factors to be considered in formulating and manufacturing a suitable product include the cleaning and polishing power of the product, its stability in its container, its appearance when dispensed, and any special manufacturing considerations.

In accordance with the present invention it is now possible to prepare and dispense a novel baking soda dentrifrice which is effective in promoting dental and oral cavity hygiene and is considered to be acceptable to the consuming public. Such product has useful cleaning, polishing and other desirable characteristics and has beneficial effects upon various parts of the human dentition (which may include the teeth and its surrounding or adjacent elements or structures, e.g., plaque, calculus, gingiva, mucous membranes, and saliva). In particular, the present toothpaste leaves the user with a clean mouth or a clean "mouthfeel effect". Due to the employment of the bi- or multi-compartmented dispensing container the product is formulatable so as to be stable upon aging or storage, without significant premature release of carbon dioxide and without undesirable separation or reaction.

U.S. Pat. Nos. 3,937,804; 3,943,240; and 4,160,022, in each of which Delaney et al. are the inventors (the disclosures of these patents and the other references mentioned later are incorporated herein by reference), describe baking soda toothpastes in which the polishing agents are composed of sodium bicarbonate with one or more of calcium carbonate (chalk), silica, alumina, zirconium silicate, sodium aluminosilicate or other compatible silicate or carbonate which is non-reactive with the bicarbonate. The "other" polishing agent is preferably calcium carbonate, which serves to stabilize the baking soda toothpaste (in which toothpaste the baking soda is in an aqueous vehicle) against substantial formation of carbon dioxide during storage. However, the same stabilizing effect may also objectionably cause a reduction in effervescence due to inhibition of the formation of carbon dioxide gas bubbles at the time the toothpaste is used.

It is an advantage of the present invention that an effervescent baking soda toothpaste is provided, which is stable on storage.

It is another advantage of this invention that an acidic agent, reactive with baking soda, is provided in a section of a toothpaste package (the dispensing container or tube) which is separate from the section containing the baking soda, in a container which is of such construction that upon extrusion of the toothpaste, the portions thereof containing the acidic agent and the baking soda are dispensed together so that they may produce effervescence during brushing of the teeth.

Further advantages are that the effervescence produced is more than that obtained when the acidic material is absent, and is about the same as results when the stabilizing polishing agent is omitted (when a non-stabilizing agent is substituted).

Other advantages of the invention will be apparent from consideration of the following specification.

In accordance with certain of its aspects this invention, which relates to a dispensing container of components of a toothpaste which effervesce in the human mouth during toothbrushing, comprises two separate toothpaste portions, which are maintained separate and out of contact with each other in different sections of the toothpaste container prior to extrusion and which are dispensable together from the container in contact with each other, the first portion comprising a vehicle containing about 5 to 35% by weight of said first portion of water and including sufficient amounts of a viscous water miscible polyol humectant and a gelling or thickening agent to impart to the portion pasty consistency, body and non-tacky nature, at least about 15% by weight of sodium bicarbonate and about 1 to 30% by weight of a water insoluble dental polishing agent which is non-reactive with sodium bicarbonate, and the second portion comprising a vehicle containing a liquid selected from the group consisting of water, viscous water miscible polyol humectant, and a mixture of water and such humectant, and about 1 to 20% by weight of said second portion of an acidic compound which has a pH of about 1.5 to 5.5 in water at a concentration in the range of 0.5 to 10% and which is reactive with said sodium bicarbonate when in contact therewith, to effervesce with formation of carbon dioxide.

In the prior art, the artisan in dentifrice manufacture has been concerned with separating reactive components in a dentifrice during storage. This is illustrated in U.S. Pat. No. 1,297,494 (No. Re. 14,961) to Rhein; U.S. Pat. No. 2,035,267 to Fleischman; U.S. Pat. No. 3,087,857 to Davis et al.; U.S. Pat. No. 3,577,521 to Scheller et al.; and British Pat. No. 1,565,672 to Goupil. In U.S. Pat. No. 1,297,494 a water-free dentifrice is described in which reaction between an acid salt and sodium bicarbonate is restrained prior to contact with saliva by the presence in the dentifrice of a neutral water-free agent, such as glycerin, or a concentrated gummy substance, such as gum arabic. In U.S. Pat. No. 2,035,267 early reaction of perborate and sodium bicarbonate in the presence of a mild acid, such as tartaric acid, in a dentifrice free of water is described as avoided by coating the perborate and bicarbonate with a stearate and coating the acid with colloidal clay. In U.S. Pat. No. 3,087,857 potassium bitartrate is described as present in a veterinary non-aqueous mouth spray containing sodium bicarbonate to permit effervescence upon contact with animal saliva. In U.S. Pat. No. 3,577,521 an acid salt is described as present in a low water content toothpaste containing a percompound to induce frothing. In British Pat. No. 1,565,672 a toothpaste is disclosed as being in two separate packages, one containing a peroxide or peroxy salt which is insoluble in water and the other containing an organic acid or acid salt. The contents of each package are maintained apart from each other until the moment of utilization. Other references of interest include U.S. Pat. Nos. 1,535,529; 3,966,863; 3,980,767; 4,066,745; and 4,328,205; and French Pat. No. 2,327,762, all of which were cited by the Examiner in Ser. No. 334,994.

The present invention is distinguishable from the prior art illustrated above since it relates to a container of dentifrice, in one part of which sodium bicarbonate has been successfully stabilized due to the presence of a suitable water insoluble dental abrasive, and in a second part of which there is contained an ingredient to induce a reaction with the previously stabilized bicarbonate and thereby provide the user with an effervescent sensation and the desirable cleaning effects of the in situ generated carbon dioxide gas. It is noteworthy that it is not necessary to avoid completely any contact between the two parts prior to the moment of utilization, as in British Pat. No. 1,565,672. Rather, compartmented toothpaste containers are used, which permit a limited and unobjectionable interfacial contact between the two portions from the time of expulsion from the container.

The portions of the toothpaste of the present invention are packaged in separate volumes of a container, from which they can be extruded simultaneously for common application to a toothbrush and brushing of the teeth. Effervescence does not occur or occurs only slightly on dispensing but with increasing contact between the sodium bicarbonate and the acidic compound as the teeth are brushed effervescence increases dramatically.

The invention will be readily understood from the present specification, taken in conjunction with the drawing, in which:

FIG. 1 is a partially centrally sectioned elevational view of a collapsible tube containing a pair of separate envelopes, each of which contains a different toothpaste portion, which envelopes terminate at the neck of the tube so that the contents thereof may be dispensed simultaneously in "striped" form;

FIG. 2 is a partial central sectional view of another dispensing tube which separates two portions of dentifrice and dispenses them together onto a toothbrush to produce a striping effect; and FIG. 3 is a central sectional view of a portion of another such dispensing tube which separates different portions of a dentifrice and dispenses them together as an attractive striped product.

In FIG. 1 dispensing tube 11, equipped with cap 13 to close it off on storage and between uses, includes a body 15 and two interior envelopes 17 and 19, which may be considered as contacting each other along surfaces 21. As illustrated, the envelopes 17 and 19 enclose compartments which contain first and second proportions 23 and 25 of an effervescent dentifrice of this invention. The threaded collar 27 on the neck portion 29 of tube 11 helps to rigidify such neck, and means, not shown, may also be provided to rigidify envelopes 17 and 19 near the neck portion, if this is considered to be desirable, although it is not necessary. As illustrated, the toothpaste will be dispensed simultaneously as two ribbons or stripes. If a multiple striping effect is desired an appropriate fitting may be inserted in the tube at the neck thereof to produce such an effect. Some such fittings are disclosed in FIGS. 1 and 3 but it is understood that they may be modified, as desired and as appropriate for particular tube designs.

In FIG. 2 there is illustrated a different embodiment of a tube for producing a striped effervescent dentifrice. Tube 31 is a modification of one shown in U.S. Pat. No. 4,211,341, with an adapter ring 33 being positioned in neck 35 thereof to produce a striping effect. Tube 31 includes wall 37, neck 35 and threaded collar 39. It contains an inner separating container 41 which is filled with a first portion of dentifrice 43. Between container 41 and wall 37 there is illustrated a second portion of dentifrice 45. The proportion of the two portions may be controllable by changing the depth of inner container 41, leaving a larger or smaller volume near the crimped bottom 47 of the collapsible tube. With adapter 33 in place in the neck of the tube the first portion of dentifrice will be completely surrounded by the second portion thereof during normal dispensing. However, as illustrated, ring 33, which inclues openings therein, such as that shown at 49, will block the flow of some of the second portion, thereby exposing the first portion at intervals over the circumference of the extruded ribbon, and producing a striping effect. As illustrated, toothpaste ribbon 51 exhibits such striping due to the use of a colorant in one of the dentifrice portions. Also as shown, the dispensed toothpaste does not expand objectionably and retains its normal shape when desposited on bristles 53 of toothbrush 55.

In FIG. 3, in which the dentifrice container is like that illustrated in U.S. Pat. No. 4,098,435, another mechanism for making a striped and effervescent dentifrice package of this invention is shown. Container 61 has in it a first dentifrice portion 63 and a second dentifrice portion 65, separated by separating means 67. It will be seen that openings 69 and 71 in fitting 73 allow the second dentifrice portion to be deposited as stripes on the first portion as it is extruded from the collapsible tube. Separator 67 may be made of any suitable material and can be positively joined to fitting 73 and envelope means (not shown) for holding dentifrice portion 63 inside tube 61. Also, to prevent any adverse reaction in the tube after the toothpaste portions come into contact with each other, neck 75 of tube 61 and the accompanying threaded collar 77 may be shortened and/or openings 69 and 71 may communicate with tubes extending "downstream" so that contact between the different portions of dentifrice is made only when such are very close to the exit from the tube.

Instead of having two portions of dentifrice dispensed together, larger numbers thereof may also be included in a single tube or other suitable multicompartmented dispenser. Thus, several colors or stripes may be used, if desired. In addition to the dispensing containers shown, others known in the art may be substituted, such as those of U.S. Pat. Nos. 2,789,731 and 3,881,529. Also, other types of dispensers, such as "aerosol" or pressurized gas activated cans may be employed. The inner surfaces of the tubes may be of lined or unlined aluminum, lined lead or plastic, and the tubes are readily collapsible, being easily compressed by hand pressing, to extrude the toothpaste portions. Upon extrusion one portion will preferably appear as a stripe or stripes on the other or as a core partially (or completely) enveloped by the other, and various other relationships of the two extruded portions are also possible.

The portions of the toothpaste present in the dispensing container are in a weight ratio of the first portion to the second portion of about 0.5:1 to 40:1, preferably about 0.7:1 to 20:1, more preferably about 0.8:1 to 5:1 and most preferably (usually) about 1:1.

The first portion of the toothpaste, that which contains the sodium bicarbonate, is stable and non-effervescent. Sodium carbonate particles are relatively soft as compared to most conventional abrasive particles used in toothpastes; nevertheless, they do exert mechanical cleaning effect on the teeth. For instance, in a radioactive dentin abrasion (RDA) test a toothpaste containing about 50 percent of bicarbonate of soda, as the sole polishing agent (or abrasive), has an RDA value of about 100 whereas when the vehicle of that toothpaste is tested (without the bicarbonate) the RDA value is only about 50.

The first portion of the toothpaste preferably usually contains at least about 15%, and preferably about 15 to 50% of sodium bicarbonate. More preferably, such percentage range is from about 20 to 40%, e.g., 30%. The sizes of the sodium bicarbonate particles may vary from coarse to fine; it is preferred that they be largely below 0.4 mm. in diameter, with a major proportion by weight being above 0.01 mm. in diameter. The vehicle in which the sodium bicarbonate particles are dispersed is aqueous, but its amount and character are preferably such that a major proportion or substantially all of the sodium bicarbonate is undissolved in the toothpaste. However, it should be understood, that when the teeth are brushed with the present toothpaste the sodium bicarbonate particles will tend to dissolve in the saliva. Such dissolving is helped by the presence of water in the toothpaste, effervescence development is speeded, and the taste and other characteristics of the toothpaste are improved, compared to dentifrices containing nonaqueous vehicle(s) only.

It is preferred for the supplementing polishing agent to be calcium carbonate (chalk). The presence of the chalk or other suitable stabilizing polishing agent produces an improvement in the stability of the bicarbonate portion of the toothpaste on aging at elevated temperatures. The addition of the compatible water insoluble polishing agent, such as chalk, silica (which designation is intended to include sodium aluminosilicate and/or silica containing combined alumina), alumina, zirconium silicate and the like, or suitable mixtures thereof, is found to yield a stable sodium bicarbonate composition, which has improved cleaning power combined with resistance to flavor separation and which does not tend to form gas on storage. In contrast, when such common dental abrasives as dicalcium phosphate or insoluble sodium metaphosphate are added to the same sodium bicarbonate compositions objectionable quantities of gas are formed, even on short term storage, e.g., one day, if the temperature is elevated. The resistance to separation out of flavoring materials in the invented products is evidenced by a decrease in the tendency for essential oils, used as flavors, to separate from the toothpaste on aging at 43° to 49° C., which separation occurs most detrimentally when the particles of sodium bicarbonate are of relatively large size, e.g., over 150 microns in diameter.

The average particle size of the chalk is preferably less than 20 microns, most preferably below 10 microns and above 1 micron. The silica may be of crystalline or amorphous type. In either case the particle size is preferably below 20 microns, e.g., 2 to 10 microns. Micronized crystalline silica or silica gel, such as the silica gels sold under the trade names Syloid 63, Syloid 74, and the like, are examples of useful silicas. The alumina may be of the hydrated or unhydrated type. For hydrated alumina the average particle size is preferably less than 20 microns, most preferably below 10 microns and above 1 or 2 microns. When zirconium silicate is employed its average particle size is preferably below 5 microns, e.g., below 3 microns and above 0.3 micron.

A particularly suitable alumina is in the form of flat flakes of alpha-alumina crystals, of disk- or plate-like configuration. Said flakes have a mean (by weight) particle diameter of less than about 7 microns, e.g., about 2 to 7 microns. The flat alpha-alumina crystals and a process for preparing them are described in U.S. Pat. No. 3,121,623. The dentifrice is preferably substantially free of anhydrous alumina particles having diameters of about 15 microns and thicknesses of about 2 microns. While it is most preferred to use alumina flakes, the mean particle diameter of which is less than five microns, e.g., about 3 to 4 microns, it is within the broader scope of this invention to use alumina flakes of larger diameters but similar thickess, such as alumina flakes that are described in the aforesaid U.S. Pat. No. 3,121,623 having average diameters of 9, 12, or 15 or more microns, free of particles over 40 microns in diameter (preferably free of particles over about 20 microns in diameter), and substantially free of particles having thicknesses above about 3 microns. In a preferred form of the invention the alpha-alumina flakes are uncoated and are nonadherent to particles of other materials. It is also within the broader scope of the invention to include other alpha-aluminas or other polishing agents of suitable hardness, sometimes about 6 on the Moh scale, in admixture with the alpha-alumina flakes. For instance, one may replace about one-half of the alumina flakes with a pulverized alpha-alumina of irregular shape and having a mean particle size of about 3 to 4 microns (with all said irregular particles being less than about 7 microns in their largest dimension). Thus, the toothpaste may contain, for example, 3% of the flakes and 2% of said irregular particles.

A typical alkali or alkaline earth metal aluminosilicate is a complex having a refractive index of about 1.45, a moisture content of about 5 to 20%, e.g., 10%, an alumina content of up to about 10%, e.g., 8%, a silica content of at least about 70%, a sodium oxide (or other alkali metal or alkaline earth metal oxide, e.g., calcium oxide) content of up to about 10%, e.g., 7%, and a particle size of below 40 microns, preferably about 1 to 20 microns.

Examples of mixtures of polishing agents are blends of chalk and hydrated alumina in equal amounts or about 25/75 or 75/25 proportions.

The composition may also contain a small amount of titanium dioxide powder, which has been found to have a marked polishing effect on the teeth when used in the sodium bicarbonate composition. The particle size of the $TiO_2$ is preferably about 0.1 to 1 micron. The weight of titanium dioxide particles in the composition is minor, from about 0.1% up to about 10% of the weight of the sodium bicarbonate, preferably about 0.1% to about 5% of the sodium bicarbonate, more preferably about 0.5 to about 1 or 2.0% thereof. The foregoing proportions of $TiO_2$ (and other components) can be readily calculated from the proportions and ratios of the other ingredients of the product, the amount of water present, (5 to 35%), the water:glycerol ratio (3:1 to 6:1), the amount of sodium bicarbonate (25 to 60%), the amount of additional polishing agent (1 to 30%), etc. For instance, the amount of TiO$_2$ present can be up to about 5 to 6%, preferably about 0.2 to 0.6% of the weight of the toothpaste, The total of polishing agent (excluding titanium dioxide) in the first portion will be about 1 to 30%, preferably 3 to 25% and more preferably 5 to 20%.

The vehicle of the first portion of the toothpaste includes a suitable liquid, preferably containing a thickening agent, e.g., a gelling agent. The vehicle is preferably aqueous but it is within the broader scope of the invention to employ non-aqueous vehicles. Generally the liquid will contain a humectant or other viscous water miscible material, such as glycerol, sorbitol, polyethylene glycol, maltitol, mannitol or any suitable mixture thereof. Water will usually constitute about 5 to 35%, e.g., about 10 to 30%, of the total vehicle of the first portion. Superior results (such as better taste) are obtained when the proportion of water is about 10 to 20% of the total of the portions of the toothpaste. Normally the sodium bicarbonate:water ratio is in the range of about 0.3:1 to 8:1 for the toothpaste, as dispensed, e.g., 0.5:1 to 3:1, but in the first toothpaste portion it may be from 0.6:1 to 10:1, often being in the range of 0.8:1 to 6:1, e.g., 3:1 to 6:1. When such or a larger proportion of water is present speedier effervescing of the toothpaste in the mouth will result.

Gelling agents for toothpaste vehicles are well known in the art. These are often high polymers, such as gums or other thickening agents, which are soluble or swellable in water or other aqueous medium. Sodium carboxymethyl cellulose has given excellent results. Other useful materials include gum tragacanth, gum arabic, gum karaya, sodium alginate, hydroxyethyl cellulose, methyl cellulose, ethyl cellulose, carrageenan and other polysaccharides, xanthan, polyvinyl pyrrollidones, thickening agents such as "Veegum" (a complex magnesium aluminum silicate) and silica aerogels. The amount of thickening agent used in the practice of this invention is preferably sufficient to impart to the mixture the pasty consistency, body and non-tacky nature which is characteristic of conventional dental creams or toothpastes. As is well known, such toothpastes are extrudable from ordinary collapsible toothpaste tubes to form a ribbon of substantial thickness, e.g., about 0.5 to 1 cm., which, if left undisturbed, substantially retains its original thickness over a period of one minute and more and does not penetrate substantially into the bristles of a toothbrush when resting on the ends of such bristles for a similar period. Such ribbons of toothpastes preferably offer substantial resistance to brushing or to deformation when, for instance, they are touched lightly with a finger. Also, such ribbons have only little tack and do not tend to form a string when the finger is pulled away from the ribbon. These properties can be helpful in preventing any objectionable premature reaction between the extruded toothpaste portions before commencement of toothbrushing. The proportion of thickening agent is often within the range of about 0.5 to 2%, such as about 0.8 to 1.5%, of the first portion of the toothpaste of this invention.

An organic surface active agent is very preferably used in the composition to aid in prophylactic action and in the thorough dispersion of the composition throughout the oral cavity, and to improve cosmetic acceptability and detersive and foaming properties. Its surface active properties help to promote reaction of the bicarbonate and acidic material, and thereby it assists in increasing the effervescence produced. Among the organic surfactants are water soluble salts of the higher alkyl sulfates, such as sodium lauryl sulfate or other suitable alkyl sulfate having 8 to 18 carbon atoms in the alkyl group; water soluble salts of sulfonated monoglycerides of higher fatty acids, such as sodium coconut monoglyceride sulfonate or other suitable sulfonated monoglyceride of a fatty acid of 10 to 18 carbon atoms; salts of amides of higher fatty acid, e.g., 12 to 16 carbon atom acids, with lower aliphatic amino acids, e.g., taurine or sarcosine, or other amino acid of 2 to 6 carbon atoms, such as sodium-N-methyl-N-palmitoyl tauride, sodium N-lauroyl-, N-myristoyl- and N-palmitoyl sarcosinates; water soluble salts of the esters of such fatty acids with isethionic acid or with glycerol monosulfate, such as the sodium salt of monosulfated monoglyceride of hydrogenated coconut oil fatty acids; water soluble salts of olefin sulfonates, e.g., alkene sulfonates or hydroxyalkene sulfonates or mixtures thereof having 12 to 16 carbon atoms in the carbon chain of the molecule; and water soluble soaps of higher fatty acids, such as those of 12 to 18 carbon atoms, e.g., coconut fatty acids. The cation of the salt may be sodium (which is preferred), potassium or mono-, di- or triethanolamine. Mixtures of surface active agents may be used. A particularly suitable mixture which provides a high foaming powder with little or no irritating effect comprises a higher alkyl sulfate and a higher fatty acid sarcosinate, e.g., in a ratio of about 1:2 to 2:1, such as about 1:1, instead of all or part of the sarcosinate a higher fatty acid monoglyceride sulfonate or other surface actie agent may be present. Also, other such mixtures of surfactants may be used.

Other suitable surface active materials include non-ionic agents, such as condensates of sorbitan monostearate with approximately 20 moles of ethylene oxide; condensates of ethylene oxide with propylene oxide condensates of propylene glycol (available under the trademark "Pluronics"); and amphoteric agents such as quaternized imidazole derivatives, which are available under the trademark "Miranol", such as Miranol C$_2$M. Cationic surface active germicides and antibacterial compounds may also be used. Such compounds include di-isobutylphenoxyethoxyethyl dimethyl benzyl ammonium chloride, benzyl dimethyl stearyl ammonium chloride, tertiary amines having one fatty alkyl group (of from 12 to 18 carbon atoms) and two (poly-)oxyethylene groups attached to the nitrogen (typically containing a total of from about 2 to 50 ethenoxy groups per molecule), salts thereof with acids, and compounds of the structure

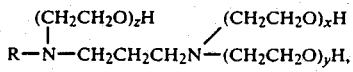

wherein R is a fatty alkyl group of about 12 to 18 carbon atoms, an x, y and z total 3 or higher, as well as salts thereof with mineral or organic acids.

It is preferred to use from about 0.05 to 5% total weight of one or more of the foregoing surface active materials in the instant dentifrice preparations. The proportion of surface active agent in the first toothpaste portion is usually within the range of about 0.05 to 5%, preferably being in the range of about 1 to 3%, such as about 1½ to 2%. While the second portion may contain similar percentages of surface active agent, often none will be used therein.

In accordance with certain aspects of this invention, cationic antibacterial agents may be included in the composition of the present invention. Such agents include:

$N^1$-(4-chlorobenzyl)-$N^5$-(2,4-dichlorobenzyl) biguanide; p-chlorophenyl biguanide;
4-chlorobenzyhydryl biguanide;
4-chlorobenzyhydrylguanylurea;
N-3-lauroxypropyl-$N^5$-p-chlorobenzylbiguanide;
1-(lauryldimethylammonium)-8-p-chlorobenzyldimethylammonium) octane dichloride;
5,6-dichloro-2-guanidinobenzimidazole;
$N^1$-p-chlorophenyl-$N^5$-laurylbiguanide;
5-amino-1,3-bis(2-ethylhexyl)-methylhexahydropyrimidine cetyl pyridimium chloride;

and their non-toxic acid addition salts, particularly the fluorides and the dihydrogen fluorides. 1,6-Di-(p-chlorophenyl-biguanidohexane) is particularly preferred. These agents may be used in amounts ranging from about 0.01 to 5% by weight of the first portion. Of course, when the first portion contains an anionic surface active agent or other anionic material that could adversely react wih the antibacterial agent, the cationic material could best be in the second portion, which would contain no such reactive component.

Any suitable flavoring or sweetening materials may be employed in formulating a flavor for the compositions of the present invention. Examples of suitable flavoring constituents include the flavoring oils, for example, oils of spearmint, peppermint, wintergreen, sassafras, clove, sage, eucalyptus, marjoram, cinnamon, lemon and orange, as well as methyl salicylate. Suitable sweetening agents include lactose, maltose, sorbitol, sodium cyclamate, perrillartine, saccharine and amoniated glycyrrhizin, e.g., as its monoammonium salt. Suitably, flavor and sweetening agent together comprise from about 0.01 to 5% or more of the composition. Preferably the amount of flavoring oil is above 0.5%, e.g., 0.7 to 2% or 0.8 to 1.2%, and the sweetening agent is from 0.1 to 4 or 0.1 to 0.5% (the latter range being for artificial sweeteners, such as saccharine).

The first portion may also contain a fluoride-containing anticaries agent. There are many water-soluble inorganic salts which are suitable sources of fluoride ions. Among these are sodium, potassium, ammonium, lithium and amine fluorides. The monofluorophosphate salts are also useful and include $Na_4P_3O_9F$, $K_4P_3O_9F$, $(NH_4)_4P_3O_9F$, $Na_3KP_3O_9F$, $(NH_4)_3NaP_3O_9F$, and $Li_4P_3O_9F$. Complex water soluble fluoride-containing salts, such as fluorosilicate $(Na_2SiF_6)$, fluorozirconate $(Na_2ZrF_6)$, fluorostannite $(KSnF_3)$, fluoroborate $(NaBF_4)$, fluorotitanate $(NaTiF_5)$, and fluorogermanate $(K_2GeF_6)$ may also be used. The fluoride ion may also be supplied by an organic fluoride which yields fluoride ions in water. Suitable such organic compounds include mono-, di-, and triethanolamine hydrofluorides. These materials are present in an effective but non-toxic amount, usually within such a range as to provide about 0.01 to 1% by weight (dentifrice basis) of the water soluble fluorine content thereof. Sodium fluoride and sodium monofluorophosphate are the preferred compounds.

Various other materials may be incorporated into the dentifrice preparations of this invention. Non-limiting examples thereof include coloring and whitening agents (some of which have been mentioned), preservatives, silicones and chlorophyll compounds, and mixtures thereof. These adjuvants are incorporated in the instant compositions in amounts which do not substantially adversely affect the properties and characteristics desired, and are selected and used in proper amounts, depending upon the particular type of preparation involved. Preferably, to make attractive striped toothpastes the coloring agent (often only 0.0001 to 0.1% of the total toothpaste, is entirely in the second portion, but this is not required. It may be in the first portion only, or in both portions, and different colors may be in such portions.

The second portion of the toothpaste of the invention, which is maintained physically separate from the first portion prior to extrusion from the toothpaste container, comprises a vehicle of a liquid selected from the group consisting of water, at least one viscous water miscible polyol humectant, and a mixture thereof, and about 1 to 20% by weight of said second portion of an acidic compound which has a pH of about 1.5 to 5.5 in water at a concentration from about 0.5 to 10%, and which is reactive with the sodium bicarbonate of the first portion when in contact therewith to cause the bicarbonate to effervesce with the formation of carbon dioxide. A preferred pH range is from about 1.5 to 3.

The vehicle most preferably includes water, glycerol, sorbitol, polyethylene glycol, maltitol, or mannitol, or any mixture thereof, as 20 to 99% by weight of the portion. The vehicle may be formulated similarly to the vehicle of the first portion, so that the two portions will be of similar apparent physical characteristics, which will permit them to be physically compatible and will allow the creation of a desirably attractive striped appearance when they are of different colors and are extruded together from a toothpaste container. In particular, amounts of gelling or thickening agent such as are present in the first portion may be present in the second portion. The second portion may optionally contain amounts of other ingredients which were described as includable in the first portion, providing that they are non-reactive with the acidic compound. Water insoluble polishing agents or abrasives which may be used in the second portion include conventional dentifrice polishing agents, such as insoluble sodium metaphosphate, dicalcium phosphate (anhydrous and/or dihydrate), and/or calcium pyrophosphate, silica (including sodium aluminosilicate or silica combined with alumina), zirconium silicate, and the like, providing that they are stable and non-reactive with the acidic compound. However, often such polishing agents will be omitted from the second portion or the proportions thereof will be less than in the first portion. The second portion of the toothpaste may be formulated as a visually clear or opaque composition, whether or not a polishing agent is present. Such effects are also obtainable for the first portion.

The degree of effervescence which is obtained when the acidic compound of the second portion comes into contact with the sodium bicarbonate of the first portion after extrusion from the toothpaste container can be adjusted by changing the ratio of the two portions to each other (useful ranges are about 0.5:1 to 40:1 or 50:1, preferably 0.7:1 to 20:1, more preferably 0.8:1 to 5:1, e.g., 1:1 by weight, of the first to the second portion), and the relative amounts of sodium bicarbonate and acidic compound present in the total toothpaste. The range of ratios may desirably be about 1:1 to 10:1 when about 20 to 40% by weight of sodium bicarbonate is in the first portion and about 4 to 10% by weight of acidic compound is in the second portion.

Acidic compounds which can be present in the second portion are malic acid, alginic acid, citric acid, succinic acid, lactic acid, tartaric acid, potassium bitartrate, acid sodium citrate, phosphoric acid and acid phosphate and pyrophosphate salts, such as monosodium phosphate and disodium pyrophosphate. The acids, and particularly organic acids, are preferred. The acidic compounds will comprise about 1 to 20% by weight of the second portion, preferably 2 to 15% and more preferably about 4 to 10% thereof.

The following examples illustrate this invention further. All proportions and amounts therein and elsewhere in this specification are by weight unless otherwise indicated.

EXAMPLE 1

An unlined aluminum toothpaste tube container is provided, containing two inner compartments, as illustrated in FIG. 1 (but the containers of FIGS. 2 and 3 may be substituted as may be those of the patents previously mentioned), such that each compartment is capable of holding a formula composition separate from the other (to prevent mixing of the two compositions in the package) and such that upon squeezing the tube, the two formula compositions in the two compartments extrude through the orifice of the tube in about a 1:1 ratio by weight. Upon extrusion one portion appears as a stripe on the other, with the toothpaste being of two such different "stripes". To make more stripes any of various fittings for the tube neck (internal baffles) may be used, such as are illustrated in the drawing, or other dispensing mechanisms, shown in the drawing and patents mentioned, may be employed.

A toothpaste of the formula of Portion 1, set forth below, is incorporated in the above described tube in the first compartment and a composition of the formula of Portion 2 is incorporated into the second compartment. The formulae of the portions are:

| COMPONENTS | PARTS (by weight) | |
|---|---|---|
| | PORTION 1 | PORTION 2 |
| Glycerol | 33.0 | 26.00 |
| Sorbitol (70%, aqueous) | — | 27.88 |
| Sodium carboxymethyl cellulose | 0.8 | — |
| Xanthan gum | — | 0.50 |
| Silica aerogel thickener* | 0.5 | 3.00 |
| Sodium benzoate (preservative) | 0.5 | 0.10 |
| Sodium saccharine | 0.2 | — |
| Silica containing combined alumina** | 17.5 | 30.00 |
| Calcium carbonate | 2.5 | — |
| Sodium bicarbonate | 20.0 | — |
| Sodium lauryl sulfate | 1.5 | — |
| Titanium dioxide | 0.4 | — |
| Malic acid | — | 4.50 |
| Flavor (essential oil mixtures plus other compounds) | 1.0 | — |
| Color (FD & C Blue No. 1, 1% aqueous solution) | — | 0.02 |
| Deionized water | Q.S. to 100.00 | Q.S. to 100.00 |

*The silica aerogel thickener is available from W.R. Grace and Company and is sold under the trade name Syloid 244.
**The silica containing combined alumina (sodium aluminosilicate) is available from J.M. Huber Corp. as Zeo 49. It can be provided in different grades. The grade used in Portion 2, makes such portion visibly clear. The grade used in Portion 1 is less suitable for visual clarity and Portion 1 contains an opacifying agent (titanium dioxide).

The pH of Portion 2, determined on the portion itself, is 2.5±0.15.

As the toothpaste is extruded from the compartmented toothpaste container, the two portions come into interfacial contact and Portion 2 appears as a clear blue stripe on the surface of Portion 1. The contact between the portions becomes intimate when the toothpaste is extruded onto a toothbrush and is used to brush the teeth and gums. Marked effervescence and effective tooth polishing occur with such contact, and the cleaning and polishing are assisted by the accompanying releases of $CO_2$ in intimate contacts with the dentition sites being treated. In the absence of Portion 2 the effervescence is much reduced and while Portion 1 alone provides effective polishing, it is with a less distinctive taste and mouth feel. The invented toothpaste has an initial salty flavor which changes during brushing (due to the effervescent reaction) to a pleasingly sweeter and flavorful minty taste. The toothpaste is sufficiently stable before brushing so that it does not distort while resting on the toothbrush prior to brushing (during the normal 1 to 1 seconds before brushing), and such stability is considered to depend, at least in part, on the presence of the stabilizing chalk and other compatible polishing agent and their effects on the bicarbonate of Portion 1. The effervescence also causes an accentuation of the flavor and improves its perception by the user.

EXAMPLES 2 AND 3

Toothpaste Portion 1 of Example 1 is incorporated into the compartmented aluminum tube container (although plastic tubes may be substituted) with each of the following Portions 2—2 and 2-3 in the other compartment (1:1 ratio):

| COMPONENTS | PARTS | |
|---|---|---|
| | PORTION 2-2 | PORTION 2-3 |
| Glycerol | 26.00 | 30.00 |
| Sorbitol (70%) | 37.38 | — |
| Xanthan gum | 1.00 | 1.00 |
| Silica aerogel (Syloid 244) | 3.00 | — |
| Sodium benzoate | 0.10 | 0.10 |
| Silica containing combined alumina*** | 20.00 | 40.00 |
| Malic acid | 4.50 | 4.50 |
| Color (FD & C Blue No. 1, 1% aqueous solution) | 0.02 | 0.04 |
| Deionized water | Q.S. to 100.00 | Q.S. to 100.00 |

***The clear grade of Zeo 49 (mentioned in Example 1) is used in Portion 2-2, which appears as a clear blue stripe on the surface of Portion 1 when the toothpaste is dispensed, and a grade of lesser clarity is used in Portion 2-3, which appears as an opaque blue stripe on the surface of Portion 1.

The pH of each of Portions 2—2 and 2-3 is 2.5±0.15.

During contact and mixing of each of Portions 2—2 and 2-3 with Portion 1 when the toothpastes are being used to brush the teeth marked effervescence occurs, which facilitates cleaning of the teeth, promotes mixings of the portions, helps to change the salty taste noted to a pleasingly sweeter flavor, and produces a unique flavor sensation in the mouth. Yet, the ribbon of toothpaste does not deform objectionably when being extruded and while resting on a toothbrush prior to use.

EXAMPLES 4-6

An amount of a composition identified as toothpaste Portion 1-4 (formula below), is incorporated into a compartment of each of three bicompartmented toothpaste containers like those illustrated in the drawing and each of equal proportions of compositions identified as Portions 2-4, 2-5 and 2-6 are packed into the other compartments of the tubes.

| COMPONENTS | PARTS PORTION 1-4 |
|---|---|
| Glycerol | 33.415 |
| Sodium carboxymethyl cellulose | 0.950 |
| Silica aerogel thickener (Syloid 244) | 0.200 |
| Sodium benzoate | 0.500 |
| Sodium saccharine | 0.200 |
| Calcium carbonate | 5.000 |
| Sodium bicarbonate | 40.000 |
| Sodium lauryl sulfate | 1.500 |
| Titanium dioxide | 0.400 |
| Flavor | 1.000 |
| Deionized water | Q.S. to 100.000 |

| COMPONENTS | PARTS PORTION 2-4 | PORTION 2-5 | PORTION 2-6 |
|---|---|---|---|
| Citric acid | 9.1 | — | — |
| Alginic acid | — | 4.8 | 9.1 |
| Deionized water | 90.9 | 95.2 | 90.9 |
| pH ±0.15 | 1.84 | 2.6 | 2.4 |

Upon extrusion from the container onto a brush, followed by intimate contact by brushing onto teeth and gums, marked effervescence occurs in each case, with the excellent cleaning effects and the pleasing taste effects and oral sensations previously mentioned.

The working examples given illustrate only some of many suitable embodiments of the invention. Of course, other humectants (or polyols), gums or thickeners, polishing agents, stabilizers, surface active agents, colorants, flavors and acidic materials may be employed in place of those shown, or various mixtures of such may be utilized. Also, the proportions given may be modified, for example, ±10% and ±25%, while still being maintained within the ranges given in the specification. The proportions of the different portions may be changed within the ranges previously given. In some instances, instead of two portions, three or more, sometimes of different colors or appearances, may be utilized. Instead of the toothpaste being dispensed from a collapsible tube, a pressurized container of suitable design may be employed. While striped toothpastes, such as those described in the working examples, or with a greater number of stripes being generated, are preferred, products having marblelized, variegated and other mixture effects are also within the invention. An important consideration is that the different reactive portions of the dentifrice should be kept separate and stable until they are to be dispensed.

Various advantages of the invention have been mentioned in the preceding specification and in the working examples but these will now be summarized and some additional desirable effects that have been noted will be set forth, too. The mentioned toothpaste tubes may be made with their compartments being integrally formed therewith, as by blow molding when plastic tubes are made. The tubes, especially if of plastic (such as those of polyethylene or polypropylene), are capable of holding both the alkaline and acidic portions of the toothpaste, so that special liners or coatings are not necessary, and presently available standard tube materials may be used. If any of the components of either portion of the toothpaste adversely reacts with a material of the tube interior it is within the invention to specially coat such interior or to line it, as with a separate tube or piece of tubing made from a material resistant to harm caused by such toothpaste portion. For example, in an aluminum tube, if the acidity of the second portion of the composition of Example 1 should be of concern, a polyethylene tube, suitable for holding half of the toothpaste (the second portion) may be inserted within the aluminum tube and when the portions are filled, such filling may be simultaneously into the aluminum tube external to the plastic tube, and into the plastic tube. In such case the plastic tube would have a built-in neck portion designed to cause it to discharge about an equal or other desired weight of the second portion along with the first portion being discharged from the aluminum tube external to the plastic tube. By modifying the outlets from the tubes or other dispensers different types of stripings or other effects are obtainable and when the acidic material is in the striping portion or composition such stripes become functional.

While the toothpaste is on the toothbrush there may be some expansion of the body of the toothpaste due to contact of the acidic material with the sodium bicarbonate, but the striping will not expand, which leads to an interesting visual effect, which can intrigue users of the product. However, the expansion of the first portion is not great and does not objectionably distort the toothpaste ribbon. Also, the striping material, rather than being merely ornamental, has become functional and by this invention one means for satisfactorily coloring or visually modifying a toothpate has also been employed for giving it another desirable effect (effervescence), without requiring additional structural changes in the dispensing container.

The effervescing dentifrice effect helps to clean the teeth and to distribute and dissolve the various components of the toothpaste. Actually, the effervescence even promotes more reaction between the bicarbonate and acidic reactant by bringing these into renewed improved contact. At the same time, it assists in separating the stabilizing material, such as chalk or other polishing agent, from the bicarbonate, so that the acidic material may react with the bicarbonate to promote more effervescence. The effervescent effects on the taste buds and sensory portion of the mouth and tongue are highly desirable. The acidic material and the carbon dioxide bubbles, together and in further conjunction with the flavoring agent(s) in the toothpaste, create a different taste effect, which is changed during the brushing of the teeth. Thus, initially such taste may be somewhat acidic, and also salty, due to the acidic material and the dissolving of the sodium bicarbonate. However, as brushing is continued the pH becomes neutral or even slightly alkaline and the flavor of the dentifrice becomes sweeter. Such flavor changes will be noted by the user and can indicate when he or she has brushed sufficiently (or insufficiently). Hopefully, the user, especially if a child, will be encouraged to continue brushing until the desired flavor change has occurred. Thus, the present dentifrices can encourge the development of good toothbrushing habits. It appears that the best combinations of acidic material, flavors and sweeteners are obtained with malic acid, alginic acid and citric acid, with spearmint, peppermint, clove and citric flavorings and with saccharine and comparable artificial sweeteners. However, other such combinations are also within the invention, preferably employing the ingredients in the given order, and mixtures of components may be used.

The invention has been described with respect to various illustrations and embodiments thereof but is not to be limited to these because it is evident that one of skill in the art, with the present specification before him, will be able to utilize substitutes and equivalents without departing from the invention.

What is claimed is:

1. A dispensing container of components of a toothpaste which does not effervesce when extruded from the container onto a toothbrush but does effervesce in the human mouth during toothbrushing, comprising two separate toothpaste portions, which are maintained in stable forms separate and substantially out of contact with each other in different parts of the container prior to extrusion and which are dispensable together from the container in contact with each other without effervescing significantly until used to brush teeth in the mouth, the first portion comprising a vehicle containing about 5 to 35 percent by weight of said first portion of water and including sufficient amounts of a viscous water miscible polyol humectant and a gelling or thickening agent to impart to the portion a pasty consistency, body and non-tacky nature, at least about 15% by weight of sodium bicarbonate and about 1 to 30% by weight of a water insoluble dental polishing agent selected from the group consisting of calcium carbonate, silica, alumina, silica containing combined alumina, zirconium silicate, and mixtures thereof, which is non-reactive with sodium bicarbonate and acts to stabilize it during storage, and the second portion comprising a vehicle containing a liquid selected from the group consisting of water, viscous water miscible polyol humectant, and a mixture of water and such humectant, and about 1 to 20% by weight of said second portion of an acidic compound which is selected from the group consisting of alginic acid, citric acid, malic acid, succinic acid, lactic acid, tartaric acid, phosphoric acid, acid phosphate salt, acid pyrophosphate salt, potassium bitartrate and sodium acid citrate, which acidic compound is of a pH of about 1.5 to 5.5 in water at a concentration in the range of 0.5 to 10%, and is reactive with sodium bicarbonate when in contact therewith, to effervesce with formation of carbon dioxide.

2. A container of effervescing toothpaste according to claim 1 wherein the container is a collapsible tube having separate compartments for the two toothpaste portions, which terminate at a tube neck portion, and in which the second portion of toothpaste contains a sufficient amount of a gelling or thickening agent to impart to such portion a pasty consistency, body and a non-tacky nature.

3. A container of effervescing toothpaste according to claim 1 wherein the weight ratio of said first portion to said second portion is in the range of 0.5:1 to 40:1.

4. A container of effervescing toothpaste according to claim 3 wherein said weight ratio is in the range of 0.7:1 to 20:1.

5. A container of effervescing toothpaste according to claim 1 wherein the first portion of toothpaste contains about 15 to 50% by weight of sodium bicarbonate, the second portion contains about 2 to 15% by weight of said acidic compound, and the weight ratio of said first portion to said second portion is in the range of 0.8:1 to 5:1.

6. A container of effervescing toothpaste according to claim 5 wherein the first portion of the toothpaste contains about 20 to 40% of sodium bicarbonate, the second portion contains about 4 to 10% of said acidic compound, the weight ratio of the first portion to the second portion is about 1:1, and the dispensed toothpaste is of a striped appearance.

7. A container of effervescing toothpaste according to claim 1 wherein said water insoluble dental polishing agent in said first portion is silica which contains combined alumina.

8. A container of effervescing toothpaste according to claim 2 wherein each of said first portion and second portion of toothpaste contains silica which contains combined alumina as a water insoluble dental polishing agent.

9. A container of effervescing toothpaste according to claim 1 wherein said acidic compound is malic acid.

10. A container of effervescing toothpaste according to claim 1 wherein said acidic compound is alginic acid.

11. A container of effervescing toothpaste according to claim 1 wherein said acidic compound is citric acid.

12. A container of effervescing toothpaste according to claim 1 wherein at least one of the portions contains a flavoring agent and one of the portions contains a sweetener, which flavoring agent produces a unique flavor sensation in the mouth of one brushing his or her teeth with the toothpaste, due to the effervescence of the toothpaste during such toothbrushing, and which sweetener, in conjunction with the flavoring agent, during such effervescence, changes the salty taste associated with sodium bicarbonate to a pleasingly sweeter flavor.

13. A container of effervescing toothpaste according to claim 12 wherein the flavoring agent and the sweetener are in the first portion of the toothpaste composition.

14. A container of effervescing toothpaste according to claim 13 wherein the flavoring agent is a mint flavor and the sweetening agent is sodium saccharin.

15. A container of effervescing toothpaste according to claim 14 wherein the acidic compound is malic acid and the compatible and stabilizing insoluble dental polishing agent is calcium carbonate.

16. A container of effervescing toothpaste according to claim 14 wherein the acidic compound is citric acid and the compatible and stablizing insoluble dental polishing agent is calcium carbonate.

* * * * *